United States Patent [19]

Fabre et al.

[11] Patent Number: 4,786,645
[45] Date of Patent: Nov. 22, 1988

[54] 1H, 3H-PYRROLO (1,2-C) THIAZOLE DERIVATIVES AND PHARMACEUTICAL COMPOSITIONS

[75] Inventors: Jean-Louis Fabre; Claude James; Daniel Lavé, all of Paris, France

[73] Assignee: Rhone-Poulenc Sante, Courbevoie, France

[21] Appl. No.: 69,211

[22] Filed: Jul. 2, 1987

[30] Foreign Application Priority Data

Jul. 4, 1986 [FR] France ............................ 86 09729

[51] Int. Cl.⁴ .................. C07D 513/04; C07D 417/14; A61K 31/44
[52] U.S. Cl. .................................... 514/333; 546/256; 546/143; 546/159; 546/270; 544/113; 544/283; 544/316; 514/259; 514/260; 514/300; 514/307; 514/311; 514/338
[58] Field of Search ................. 546/270, 256; 514/333

[56] References Cited

U.S. PATENT DOCUMENTS 4,529,728 7/1985 Fabre et al. .................... 546/256

FOREIGN PATENT DOCUMENTS 0115979 1/1984 France ............................ 546/256

Primary Examiner—Mary C. Lee
Assistant Examiner—Zinna Northington
Attorney, Agent, or Firm—Stevens, Davis, Miller & Mosher

[57] ABSTRACT

A compound of the general formula I:

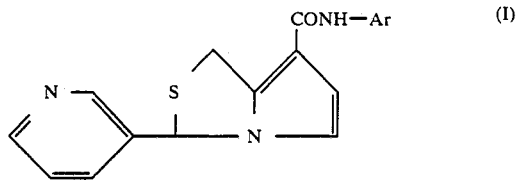

in which Ar is a pyridyl, quinolinyl, isoquinolinyl, naphthyridinyl, pyrimidyl, quinazolinyl, thiazolyl, benzothiazolyl, imidazolyl, benzimidazolyl, oxazolyl, benzoxazolyl, thienyl, benzothienyl or naphthyl group; optionally substituted with one or more halogen or alkyl, alkyloxy, alkylthio, trifluoromethyl, amino, alkylamino, dialkylamino, hydroxy, cyano, alkylsulphinyl, alkylsulphonyl, sulphamido, alkylsulphamido, dialkylsulphamido, alkylcarbonyl, benzoyl, alkyloxycarbonyl, carboxy, phenoxycarbonyl, alkylcabonyloxy, benzoyloxy, alkylcarbonylamino, benzamido, phenyl, benzyl, phenoxy or phenylthio group, provided that (i) when Ar is a pyridyl group, the pyridyl group must be substituted, (ii) an alkyl moiety contains 1 to 4 straight- or branched chain carbon atoms; (iii) a phenyl moiety may be unsubstituted or substituted with one or more halogen or alkyl, alkyloxy, alkylthio, trifluoromethyl, amino, alkylamino, dialkylamino, hydroxy, cyano, phenyl or benzyl group in separate enantiomeric form or mixtures thereof, or a pharmaceutically acceptable salt thereof is useful in the treatment of all pathological conditions in which PAF-acether may be implicated directly or indirectly.

12 Claims, No Drawings

1H, 3H-PYRROLO (1,2-C) THIAZOLE DERIVATIVES AND PHARMACEUTICAL COMPOSITIONS

The present invention provides compounds of the general formula I:

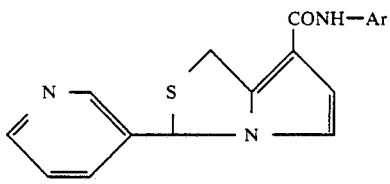

in which Ar is a pyridyl, quinolinyl, isoquinolinyl, naphthyridinyl, pyrimidyl, quinazolinyl, thiazolyl, benzothiazolyl, imidazolyl, benzimidazolyl, oxazolyl, benzoxazolyl, thienyl, benzothienyl or naphthyl group; optionally substituted with one or more halogen or alkyl, alkyloxy, alkylthio, trifluoromethyl, amino, alkylamino, dialkylamino, hydroxy, cyano, alkylsulphinyl, alkylsulphonyl, sulphamido, alkylsulphamido, dialkylsulphamido, alkylcarbonyl, benzoyl, alkyloxycarbonyl, carboxy, phenoxycarbonyl, alkylcarbonyloxy, benzoyloxy, alkylcarbonylamino, benzamido, phenyl, benzyl, phenoxy or phenylthio group, provided that (i) when Ar is a pyridyl group, the pyridyl group must be substituted, (ii) an alkyl moiety contains 1 to 4 straight- or branched chain carbon atoms; (iii) a phenyl moiety may be unsubstituted or substituted with one or more halogen or alkyl, alkyloxy, alkylthio, trifluoromethyl, amino, alkylamino, dialkylamino, hydroxy, cyano, phenyl or benzyl group
in separate enantiomeric form or mixtures thereof, or a pharmaceutically acceptable salt thereof.

According to one aspect of the invention, the compounds of general formula (I) may be prepared by reacting an amine of general formula $$ArNH_2 \qquad (II)$$

in which Ar is defined as above, with an acid of formula:

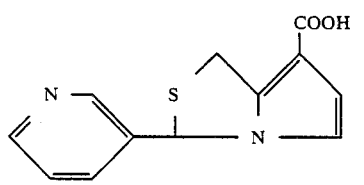

or a reactive derivative of this acid, isolating the product and, if required, converting it into a pharmaceutically acceptable salt.

In fact, it is particularly advantageous to use the acid of formula (III) in an activated form such as the acid chloride or to react it with N,N'-carbonyldiimidazole or an alkyl chloroformate before condensing the amine of general formula (II).

It is generally preferable to use the acid chloride and to carry out the reaction in an organic solvent such as chloroform, methylene chloride or dioxane at a temperature between 0° C. and the reflux temperature of the reaction mixture, in the presence of an acceptor for acid such as triethylamine.

The racemic acid of formula (III) may be prepared according to the method described in European Patent No. 0,115,979.

The amines of general formula (II) may be prepared by applying or adapting the methods already described in the literature.

Because of the presence of an asymmetric carbon atom in position 3 of the pyrrolo[1,2-c]thiazole ring, the compounds of general formula (I) according to the invention can exist in the racemic form or in the form of enantiomers. The method described above generally leads to racemic products, but it is understood that the corresponding enantiomers may be obtained directly if the method is implemented operating with an acid of formula (III) which is optically active.

The optically active form of the acid of formula (III) may be prepared as follows:

A. First method: an optically active ester with a corresponding specific rotation, of the following general formula:

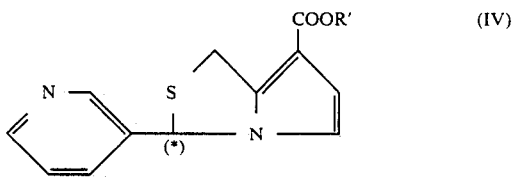

in which R' represents an alkyl radical containing 1 to 4 carbon atoms in straight- or branched-chain and the symbol * indicates the asymmetric atom, the compound employed being dextrorotatory or levorotatory, is saponified.

The saponification is generally carried out by any mild method known to the person skilled in the art for the conversion of an ester into an acid without racemizing the chiral centres present in the molecule. It is particularly advantageous to carry out the saponification using an alkali metal hydroxide such as sodium hydroxide or potassium hydroxide at a temperature between 20° and 50° C.

The ester of general formula (IV) may be obtained by reacting the reaction product of p-toluenesulphonyl chloride, triethylamine and the acid of formula:

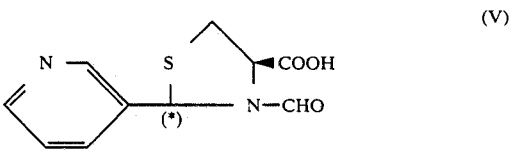

in which the symbol * has the same meaning as in the corresponding ester (IV) defined above, with the reaction product of triethylamine and an alkyl 2,3-dichloropropionate of general formula:

in which R' is defined as above, in an organic solvent such as 1,2-dichloroethane or methylene chloride at a temperature between 20° C. and the reflux temperature of the reaction mixture.

The acid of general formula (V) may be obtained by reacting a mixture of formic acid and acetic anhydride with an acid of formula:

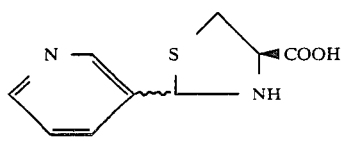

(VII)

and subsequently separating the dextrorotatory and levorotatory forms operating according to conventional methods, e.g. by recrystallization and/or salt formation with optically active bases such as α-methylbenzylamine, separation of these salts and the release of the corresponding acid.

B. Second method: the enantiomers of the acid of formula (III) are separated by any method known to the person skilled in the art, especially by salt formation with an optically active base such as the optically active forms of α-methylbenzylamine, recrystallization of the salt obtained and decomposition of the latter with an acid such as hydrochloric acid.

The compounds of general formula (I) which may be dextrorotatory, levorotatory or racemic, may also be prepared by reacting p-toluenesulphonyl chloride, triethylamine and a racemic or optically active acid of formula V:

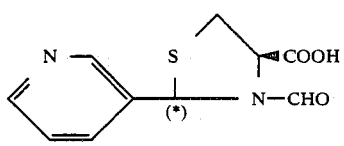

(V)

in which the symbol * indicates the asymmetric atom and reacting the product of this with the reaction product of triethylamine and a compound of general formula VIII:

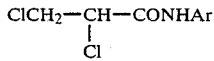

(VIII)

in which Ar is as defined above optionally in protected form, isolating the product, removing any protecting groups present, and, if required, converting the product to a pharmaceutically acceptable salt.

The reaction is generally carried out in an organic solvent such as 1,2-dichloroethane or methylene chloride at a temperature between 20° C. and the reflux temperature of the reaction mixture.

The compounds of general formula (VIII) may be prepared by applying or adapting known methods in the literature, especially by reacting 2,3-dichloropropionyl chloride with an amine of general formula (II) defined as above, operating in toluene at a temperature between 20° C. and the reflux temperature of the reaction mixture.

It is understood that, in order to implement the method described above, it may be necessary to introduce protective groups for some groups present in the radical Ar of the different compounds employed. The protective group may later be removed at the most appropriate stage in the synthesis. Thus, when the radical Ar contains an amino or alkylamino group, the latter may be protected, e.g. with a tert-butyl-oxycarbonyl radical and later released after reacting with an aqueous acid, e.g. with an aqueous hydrochloric acid solution, or preferably with a solution containing hydrogen chloride gas dissolved in acetic acid. When the radical Ar contains a hydroxy group, the latter may advantageously be protected in the form of a tetrahydropyranyloxy or methoxymethyloxy radical and later released, after reaction involving hydrolysis. When the radical Ar contains a carboxyl group, the latter may advantageously be protected in the form of an alkyl ester which could be saponified to give the corresponding acid, according to conventional methods.

The compounds of general formula (I) may be converted into addition salts with acids by reacting with an acid in an organic solvent such as an alcohol, a ketone, an ether or a chlorinated solvent. The salt precipitates, generally on concentrating the solution thereof; it is separated by filtration or decantation.

The compounds of general formula (I) which contain an acid group in their molecule may be converted into metal salts or into addition salts with nitrogenous bases, by any method known to the person skilled in the art for carrying out this salification without disturbing the rest of the molecule.

When a compound identified by its chemical name is referred to in the present description, if the type of isomer is not specifically mentioned, it is understood that it always refers to the corresponding racemic compound.

The compounds according to the invention and their addition salts have useful pharmacological properties combined with a low toxicity. They prove to be active at inhibitory concentrations ($IC_{50}$) of between 1 and 1,000 nM in the antagonism test for the binding of [$^3$H]-1-0-octadecyl-2-0-acetyl-3-ns-glycerophosphorylcholine tritiated P.A.F.-acether [platelet activating factor]) to its receptor sites on blood platelets according to the following technique:

(a) Preparation of washed rabbit platelets.

Male New Zealand rabbits (hybrid HY 2000) weighing approximately 2.5 kg are punctured in the auricular artery. Blood is collected into a mixture of citric acid (1.9 mM), trisodium citrate (9 mM), monosodium phosphate (1.75 mM) and dextrose (5.6 mM). The blood is centrifuged at 150 g for 20 minutes at 15° C. Plateletrich plasma (PRP) is thereby obtained. This plasma is centrifuged at 1000 g for 15 minutes at 15° C. The platelet pellet thus obtained is washed first with modified Tyrode's solution containing 0.35% bovine serum albumin (BSA), 2 mMole $MgCl_2$, 0.2 mMole of EGTA, and then with a Tyrode's solution without EGTA. The platelets are finally suspended in a trial buffer (buffer A) with the following composition: NaCl (140 mM), KCl (2.7 mM), $NaH_2PO_4$ (0.4 mM), $MgCl_2$ (2 mM), $NaHCO_3$ (12 mM), tris-HCl buffer (10 mM), dextrose (6.2 mM) and BSA (0.25%). The final concentration of the suspension is adjusted to $4 \times 10^8$ platelets/cc with this buffer.

(b) Performance of the actual test.

The buffer A described above, the product under study, the triatiated PAF-acether (0.5 nMole; specific activity: 80 Ci/mMole) and the platelets obtained as described above ($0.5 \times 10^8$ platelets) are introduced successively into a 5 cc tube so as to obtain a final volume of 0.5 cc and the mixture is incubated for one hour at 20° C. Buffer A (2 cc), cooled to 4° C., is then added and the contents of the tube are quickly filtered through a WHATMAN GF/C (trade mark) filter and the tube is very quickly rinsed with buffer A (3×2 cc) cooled to 4° C. The filter is dried and placed in a vial containing the liquid scintillant READY SOLV. MP (T. M. BECKMAN) (4.5 cc) and the radioactivity is measured with an LKB RACK BETA 1218 universal counter. The total bound radioactivity is thus determined.

The specific binding of the tritiated PAF-acether is determined by subtracting the radioactivity remaining on the filter after adding 10 μmole of N-(3-methoxyphenyl)-3-(3-pyridyl)-1H,3H-pyrrolo[1,2-c]thiazole-7-carboxamide from the total bound radioactivity. For each product under study, the trial is repeated 3 times at increasing concentrations ranging from $10^{-10}$ to $10^{-4}$ M. For each product, the $IC_{50}$ is determined graphically by the log Probit analysis of the inhibition curve.

It is known that PAF-acether is involved in a Large number of diseases and disorders such as allergic reactions (asthma or bronchitis) or inflammatory reactions of the gastric and intestinal mucosae of different origins and especially the inflammatory reactions caused by radiations and by endotoxin-induced shocks and disorders related to platelet aggregation. The PAF-acether released during these disorders become bound to the specific receptors of this mediator. The test for binding to blood platelet receptors described above is one of the possible experimental models for studying the capacity of the products to bind themselves to these receptors.

The products according to the invention displace the PAF-acether from their binding sites. Therefore they enter into competition with it and antagonize the effects thereof. Thus, the compounds according to the invention have a therapeutic role in the treatment of the diseases and the conditions listed above.

Pyrrolothiazoles which have a certain inhibitory effect towards PAF-acether are already known from European patent No. 0,115,979, but the compounds according to the present invention become bound to platelet receptors at much lower doses and are therefore more effective at inhibiting the effects of PAF-acether.

Moreover, the compounds according to the invention have a low toxicity. Their oral $LD_{50}$ is generally between 300 and 900 mg/kg in mice.

The compounds of general formula (I) in which Ar represents a pyridyl or naphthyl radical optionally substituted with one or more halogen atoms or alkyl or alkyloxy radicals, provided that when Ar represents a pyridyl radical, the latter is necessarily substituted, are particularly valuable.

The compounds of general formula (I) in which Ar represents a pyridyl radical substituted with a halogen atom or an alkyl radical are more particularly valuable.

The following compounds are of a very particular value:
(+)-N-(4-methyl-2-pyridyl)-3-(3-pyridyl)-1H,3H-pyrrolo[1,2-c]thiazole-7-carboxamide
N-(4-methyl-2-pyridyl)-3-(3-pyridyl)-1H,3H-pyrrolo[1,2-c]thiazole-7-carboxamide
N-(6-chloro-2-pyridyl)-3-(3-pyridyl)-1H,3H-pyrrolo[1,2-c]thiazole-7-carboxamide and
N-(4-chloro-2-pyridyl)-3-(3-pyridyl)-1H,3H-pyrrolo[1,2-c]thiazole-7-carboxamide.

In general, the compounds according to the invention which are most valuable are those which are in the racemic form and the optical isomers of the dextrorotatory form.

For therapeutic use, the compounds of general formula (I) may be used as such or, when appropriate, in the form of pharmaceutically acceptable salts, i.e. salts which are non-toxic at the doses of use.

As pharmaceutically acceptable salts, there may be mentioned addition salts with inorganic acids, such as hydrochlorides, sulphates, nitrates and phosphates or with organic acids, such as acetates, propionates, succinates, benzoates, fumarates, malates, methanesulphonates, isethionates, theophillineacetates, salicylates, phenolphtalinates, methylene-bis-β-oxynaphthoates or the substitution derivatives of these compounds.

There may also be mentioned, when they can exist, alkali metal salts such as sodium, potassium or lithium salts or alkaline earth metal salts such as calcium or magnesium salts and addition salts with organic bases such as ethanolamine or lysine salts.

The following examples show how the invention can be put into practice.

EXAMPLE 1

7-Chloroformyl-3-(3-pyridyl)-1H,3H-pyrrolo[1,2-c]thiazole hydrochloride (9 g) is added, at a temperature between 60° and 68° C., to a solution of 2-amino-6-chloropyridine (3.9 g) and triethylamine (6.1 g) in dioxane (200 cc) which is heated to a temperature in the vicinity of 60° C., in the course of 5 minutes. The suspension obtained is heated, with stirring, at a temperature in the vicinity of 100° C. for 5 hours and 45 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (500 cc). The solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 50° C. A crude product (9.5 g) is thereby obtained, which is dissolved in boiling butan-1-ol (140 cc). Decolorizing charcoal (0.5 g) is added to the solution obtained and the suspension is filtered in the heated state. The filtrate is cooled at a temperature in the vicinity of 4° C. for 16 hours. The crystals formed are separated by filtration, washed 3 times with butan-1-ol (30 cc in total) and 3 times with diethyl ether (150 cc in total) and then dried under reduced pressure (20 mm Hg; 2.7 kPa) at a temperature in the vicinity of 20° C. in the presence of potassium hydroxide pellets. N-(6-chloro-2-pyridyl)-3-(3-pyridyl)-1H, 3H-pyrrolo[1,2-c]thiazole-7-carboxamide (5,6 g) in the form of cream-coloured crystals, m.p. 186° C., is thereby obtained.

The 2-amino-6-chloropyridine may be prepared according to J. P. WIBAUT and J. R. NICOLAI, Rec. Trav. Chim., 58, 709 (1939).

The 7-chloroformyl-3-(3-pyridyl)-1H,3H-pyrrolo[1,2-c]thiazole hydrochloride is prepared according to the method described in European patent No. 0,115,979.

EXAMPLE 2

7-Chloroformyl-3-(3-pyridyl)-1H,3H-pyrrolo[1,2-c]thiazole hydrochloride (12 g) is added, at a temperature between 60° and 70° C., to a solution of 2-amino-6-fluoropyridine (4.5 g) and triethylamine (8.1 g) in dioxane (250 cc) which is heated to a temperature in the vicinity of 60° C., in the course of 5 minutes. The suspension obtained is heated at a temperature in the vicinity of 100° C. for 6 hours and 45 minutes and then stirred at a temperature in the vicinity of 20° C. for 16 hours. The solvent is evaporated off under reduced pressure (20 mm Hg; 2.7 kPa) at a temperature in the vicinity of 60° C. The residue obtained is dissolved in methylene chloride (500 cc) and the solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 50° C. A crude product (11.4 g) is thereby obtained, which is dissolved in boiling butan-1-ol (70 cc). Decolorizing charcoal (0.5 g) is added to the solution obtained and the suspension is filtered in the heated state. The filtrate is cooled at a temperature in the vicinity of 4° C. for 2 hours. The crystals formed are separated by filtration, washed 3 times with butan-1-ol (45 cc in total), twice with ethanol (50 cc in total) and 3 times with diethyl ether (90 cc in total) and then dried under the reduced pressure (20 mm Hg; 2.7 kPa) at a temperature in the vicinity of 20° C. in the presence of potassium hydroxide pellets. N-(6-fluoro-2-pyridyl)-3-(3-pyridyl)-1H,3H-pyrrolo[1,2- c]thiazole-7-carboxamide (5.3 g) in the form of beige-coloured crystals, m.p. 198° C., is thereby obtained.

The 2-amino-6-fluoropyridine may be prepared according to the method described in British Patent No. 2,078,738.

The 7-chloroformyl-3-(3-pyridyl)-1H,3H-pyrrolo[1,2-c]thiazole hydrochloride is prepared according to the method described in European Patent No. 0,115,979.

EXAMPLE 3

7-Chloroformyl-3-(3-pyridyl)-1H,3H-pyrrolo[1,2-c]thiazole hydrochloride (6 g) is added, at a temperature between 60° and 66° C., to a solution of 2-amino-6-picoline (2.2 g) and triethylamine (4.05 g) in dioxane (130 cc) which is heated to a temperature in the vicinity of 60° C., in the course of 5 minutes. The suspension obtained is heated, with stirring, at a temperature in the vicinity of 100° C. for 7 hours and 30 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (300 cc) and the solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 60° C. A crude product (5.6 g) is thereby obtained, which is dissolved in boiling acetonitrile (60 cc). Decolorizing charcoal (0.5 g) is added to the solution obtained and the suspension is filtered in the heated state. The filtrate is cooled at a temperature in the vicinity of 4° C. for 2 hours. The crystals formed are separated by filtration, washed twice with acetonitrile cooled to a temperature in the vicinity of 4° C. (20 cc in total) and then twice with diethyl ether (50 cc in total) and dried under reduced pressure (20 mm Hg; 2.7 kPa) at a temperature in the vicinity of 20° C. in the presence of potassium hydroxide pellets. N-(6-methyl-2-pyridyl)-3-(3-pyridyl)-1H,3H-pyrrolo[1,2-c]thiazole-7-carboxamide (2.5 g) in the form of beige-coloured crystals, m.p. 162° C., is thereby obtained.

The 7-chloroformyl-3-(3-pyridyl)-1H,3H-pyrrolo[1,2-c]thiazole hydrochloride is prepared according to the method described in European Patent No. 0,115,979.

EXAMPLE 4

7-Chloroformyl-3-(3-pyridyl)-1H,3H-pyrrolo[1,2-c]thiazole hydrochloride (6 g) is added, at a temperature in the vicinity of 40° C., to a solution of 2-amino-6-methoxypyridine (2.5 g) and triethylamine (4.1 g) in dioxane (80 cc) which is heated to a temperature in the vicinity of 40° C., in the course of 15 minutes. The suspension obtained is heated, with stirring, at a temperature in the vicinity of 100° C. for 6 hours and then stirred at a temperature in the vicinity of 20° C. for 12 hours. The solvent is evaporated off under reduced pressure (20 mm Hg; 2.7 kPa) at a temperature in the vicinity of 60° C. The residue is dissolved in methylene chloride (300 cc) and the solution obtained is washed twice with distilled water (200 cc in total), twice with an aqueous 2N sodium hydroxide solution (200 cc in total) and 5 times with distilled water (500 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 50° C. A product (5.6 g) is thereby obtained, which is chromatographed on a 6 cm diameter column containing silica (0.04–0.063 mm; 480 g). Elution is carried out with a mixture of ethyl acetate and methanol (95:5 by volume) at a pressure of 0.4 bar (41 kPa), collecting 75 cc fractions. The first 9 fractions are discarded. The following 6 fractions are combined and concentrated to dryness under reduced pressure (20 mm Hg; 2.7 kPa) at a temperature in the vicinity of 50° C. A crude product (3.6 g) with a melting point of 151° C. is thereby obtained. This product is dissolved in boiling ethanol (50 cc). Decolorizing charcoal (0.5 g) is added to the solution obtained and the suspension is filtered in the heated state. The filtrate obtained is cooled at a temperature in the vicinity of 4° C. for 2 hours. The crystals formed are separated by filtration, washed twice with ethanol cooled to a temperature in the vicinity of 4° C. (10 cc in total) and twice with diethyl ether (20 cc in total) and then dried under reduced pressure (20 mm Hg; 2.7 kPa) at a temperature in the vicinity of 20° C. in the presence of potassium hydroxide pellets. N-(6-methoxy-2-pyridyl)-3-(3-pyridyl)-1H,3H-pyrrolo[1,2-c]thiazole-7-carboxamide (3 g) in the form of white crystals, m.p. 154° C., is thereby obtained.

The 2-amino-6-methoxypyridine may be prepared according to A. F. BICKEL and J. P. WIBAUT, Rec. Trav. Chim., 65, 65 (1946).

The 7-chloroformyl-3-(3-pyridyl)-1H,3H-pyrrolo[1,2-c]thiazole hydrochloride is prepared according to the method described in European Patent No. 0,115,979.

EXAMPLE 5

7-Chloroformyl-3-(3-pyridyl)-1H,3H-pyrrolo[1,2-c]thiazole hydrochloride (6 g) is added, at a temperature between 60° and 65° C., to a solution of 1-naphthylamine (2.9 g) and triethylamine (4.1 g) in dioxane (100 cc) which is heated to a temperature in the vicinity of 60° C., in the course of 5 minutes. The suspension obtained is heated, with stirring, at a temperature in the vicinity of 100° C. for 5 hours and then stirred at a temperature in the vicinity of 20° C. for 16 hours. The solvent is evaporated off under reduced pressure (20 mm Hg; 2.7 kPa) at a temperature in the vicinity of 60° C. The residue obtained is dissolved in methylene chloride (300 cc) and the solution obtained is washed twice with distilled water (200 cc in total), twice with an aqueous 2N sodium hydroxide solution (200 cc in total) and twice with distilled water (200 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 60° C. A crude product is thereby obtained (7.5 g). This product is dissolved in boiling ethanol (50 cc). Decolorizing charcoal (0.5 g) is added to the solution obtained and the suspension is filtered in the heated state. The filtrate is cooled at a temperature in the vicinity of 4° C. for 16 hours. The crystals formed are separated by filtration, washed twice with ethanol (20 cc in total), 3 times with diethyl ether (90 cc in total) and dried under reduced pressure (20 mm Hg; 2.7 kPa) at a temperature in the vicinity of 20° C. in the presence of potassium hydroxide pellets. A product (3.9 g) with a melting point of 135° C. is thereby obtained. A part of this product (3.7 g) is dissolved in boiling isopropanol (55 cc). The solution obtained is filtered in the heated state. The filtrate is cooled at a temperature in the vicinity of 4° C. for 16 hours. The crystals formed are separated by filtration, washed twice with isopropanol (10 cc in total) and then 3 times with diethyl ether (45 cc in total) and dried under reduced pressure (20 mm Hg; 2.7 kPa) at a temperature in the vicinity of 20° C. in the presence of potassium hydroxide pellets. N-(1-naphthyl)-3-(3-pyridyl)-1H,3H-pyrrolo[1,2-c]thiazole-7-carboxamide (3.3 g) in the form of cream-coloured crystals, m.p. 136° C., is thereby obtained.

The 7-chloroformyl-3-(3-pyridyl)-1H,3H-pyrrolo[1,2-c]thiazole hydrochloride is prepared according to the method described in European Patent No. 0,115,979.

EXAMPLE 6

7-Chloroformyl-3-(3-pyridyl)-1H,3H-pyrrolo[1,2-c]thiazole hydrochloride (6 g) is added, at a temperature in the vicinity of 67° C., to a solution of 2-amino-4-chloropyridine (2.6 g) and triethylamine (4.05 g) in dioxane (150 cc) which is heated to a temperature in the vicinity of 67° C., in the course of 15 minutes. The suspension obtained is heated, with stirring, at a temperature in the vicinity of 100° C. for 7 hours and 30 minutes and then stirred at a temperature in the vicinity of 20° C. for 16 hours. The solvent is evaporated off under reduced pressure (20 mm Hg; 2.7 kPa) at a temperature in the vicinity of 60° C. The residue obtained is dissolved in methylene chloride (350 cc). The solution obtained is washed twice with distilled water (200 cc in total), twice with an aqueous 1N sodium hydroxide solution (200 cc in total) and 3 times with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 50° C. A crude product (5 g) is thereby obtained, which is dissolved in boiling acetonitrile (200 cc). Decolorizing charcoal (0.5 g) is added to the solution obtained and the suspension is filtered in the heated state. The filtrate is cooled at a temperature in the vicinity of 4° C. for 2 hours. The crystals formed are separated by filtration, washed twice with acetonitrile cooled to a temperature in the vicinity of 4° C. (10 cc in total) and twice with diethyl ether (20 cc in total) and then dried under reduced pressure (20 mm Hg; 2.7 kPa) at a temperature in the vicinity of 20° C. in the presence of potassium hydroxide pellets. N-(4-chloro-2-pyridyl)-3-(3-pyridyl)-1H,3H-pyrrolo[1,2-c]thiazole-7-carboxamide (2.6 g) in the form of cream-coloured cyrstals, m.p. 190° C., is thereby obtained.

The 2-amino-4-chloropyridine may be obtained according to R. GRAF, Chem. Ber., 64, 21 (1931).

The 7-chloroformyl-3-(3-pyridyl)-1H,3H-pyrrolo[1,2-c]thiazole hydrochloride is prepared according to the method described in European Patent No. 0,115,979.

EXAMPLE 7

7-Chloroformyl-3-(3-pyridyl)-1H,3H-pyrrolo[1,2-c]thiazole hydrochloride (6 g) is added, at a temperature between 68° and 75° C., to a solution of 2-amino-6-ethylpyridine (2.45 g) and triethylamine (4.05 g) in dioxane (150 cc) which is heated to a temperature in the vicinity of 68° C., in the course of 5 minutes. The suspension obtained is heated, with stirring, at a temperature in the vicinity of 100° C. for 6 hours and 15 minutes and then stirred at a temperature of 20° C. for 16 hours. The solvent is evaporated off under reduced pressure (20 mm Hg; 2.7 kPa) at a temperature in the vicinity of 60° C. The residue is dissolved in methylene chloride (300 cc). The solution obtained is washed twice with distilled water (300 cc in total), twice with an aqueous 2N sodium hydroxide solution (300 cc in total) and twice with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 60° C. A crude product (6.5 g) is thereby obtained, which is dissolved in boiling acetonitrile (75 cc). Decolorizing charcoal (0.5 g) is added to the solution obtained and the suspension is filtered in the heated state. The filtrate is cooled at a temperature in the vicinity of 4° C. for 16 hours. The crystals formed are separated by filtration, washed twice with acetonitrile cooled to a temperature in the vicinity of 4° C. (10 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-(6-ethyl-2-pyridyl)-3-(3-pyridyl)-1H,3H-pyrrolo[1,2-c]thiazole-7-carboxamide (2.3 g) in the form of cream-coloured crystals, m.p. 150° C., is thereby obtained.

The 2-amino-6-ethylpyridine may be prepared according to S. J. CHILDRESS and J. V. SCUDI, J. Org. Chem., 23, 67 (1958).

The 7-chloroformyl-3-(3-pyridyl)-1H,3H-pyrrolo[1,2-c]thiazole hydrochloride is prepared according to the method described in European Patent No. 0,115,979.

EXAMPLE 8

7-Chloroformyl-3-(3-pyridyl)-1H,3H-pyrrolo[1,2-c]thiazole hydrochloride (6 g) is added, at a temperature between 70° and 76° C., to a solution of 3-methyl-1-naphthylamine hydrochloride (3.9 g) and triethylamine (6.1 g) in dioxane (200 cc) which is heated to a temperature in the vicinity of 70° C., in the course of 5 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (500 cc) and the solution obtained is washed twice with distilled water (400 cc in total), twice with an aqueous 2N sodium hydroxide solution (400 cc in total) and twice with distilled water (400 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 60° C. A product (7.6 g) is thereby obtained, which is chromatographed on a 6 cm diameter column containing silica (0.02–0.045 mm; 480 g). Elution is carried out with ethyl acetate:cyclohexane mixtures at a pressure of 0.4 bar (41 kPa), collecting 200 cc fractions. The first 14 fractions originating from elution with an ethyl acetate:cyclohexane (80:20 by volume) mixture are discarded. The following 11 fractions originating from elution with an ethyl acetate:cyclohexane (80:20 by volume) mixture and the following 7 fractions originating from elution with ethyl acetate are combined and concentrated to dryness under reduced pressure (20 mm Hg; 2.7 kPa) at a temperature in the vicinity of 60° C. A crude product (6.8g) with a melting point of 170° C. is thereby obtained. This product is dissolved in boiling acetonitrile (50 cc). Decolorizing charcoal (0.5 g) is added to the solution obtained and the suspension is filtered in the heated state. The filtrate obtained is cooled at a temperature in the vicinity of 4° C. for 16 hours. The crystals formed are separated by filtration, washed twice with acetonitrile (30 cc in total) and 3 times with diethyl ether (90 cc in total) and then dried under reduced pressure (20 mm Hg; 2.7 kPa) at a temperature in the vicinity of 20° C. in the presence of potassium hydroxide pellets. N-(3-methyl-1-naphthyl)-3-(3-pyridyl)-1H,3H-pyrrolo[1,2-c]thiazole-7-carboxamide (3.5 g) in the form of pale yellow crystals, m.p. 172° C., is thereby obtained.

The 3-methyl-1-naphthylamine hydrochloride may be prepared according to N. P. BUU-HOI, M. MANGANE and P. JACQUIGNON, J. Chem. Soc., C, 662 (1967).

The 7-chloroformyl-3-(3-pyridyl)-1H,3H-pyrrolo[1,2-c]thiazole hydrochloride is prepared according to the method described in European Patent No. 0,115,979.

EXAMPLE 9

7-Chloroformyl-3-(3-pyridyl)-1H,3H-pyrrolo[1,2-c]thiazole hydrochloride (6 g) is added, at a temperature between 65° and 72° C., to a solution of 2-amino-4-methylpyridine (2.15 g) and triethylamine (4.05 g) in dioxane (100 cc) which is heated to a temperature in the vicinity of 65° C., in the course of 20 minutes. The suspension obtained is heated, with stirring, at a temperature in the vicinity of 100° C. for 5 hours and 45 minutes and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (250 cc). The solution obtained is washed with distilled water (100 cc) and then with an aqueous 4N sodium hydroxide solution (100 cc) and 3 times with distilled water (450 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 50° C. A crude product (4.8 g) is thereby obtained, which is dissolved in boiling acetonitrile (50 cc). Decolorizing charcoal (0.5 g) is added to the solution obtained and the suspension is filtered in the heated state. The filtrate is cooled at a temperature in the vicinity of 4° C. for 1 hour. The crystals formed are separated by filtration, washed twice with acetonitrile cooled to a temperature in the vicinity of 4° C. (10 cc in total) and then dried under reduced pressure (20 mm Hg; 2.7 kPa) at a temperature in the vicinity of 20° C. in the presence of potassium hydroxide pellets. N-(4-methyl-2-pyridyl)-3-(3-pyridyl)-1H,3H-pyrrolo[1,2-c]thiazole-7-carboxamide (1.5 g) in the form of cream-coloured crystals, m.p. 163° C., is thereby obtained.

7-Chloroformyl-3-(3-pyridyl)-1H,3H-pyrrolo[1,2-c]thiazole hydrochloride is prepared according to the method described in European Patent No. 0,115,979.

EXAMPLE 10

The hydrochloride of the acid chloride derived from (+)-3-(3-pyridyl)-1H,3H-pyrrolo[1,2-c]thiazole-7-carboxylic acid (12 g) is added, at a temperature between 65° and 72° C., to a solution of 2-amino-4-methylpyridine (4.3 g) and triethylamine (8.1 g) in dioxane (300 cc) which is heated to a temperature in the vicinity of 60° C., in the course of 5 minutes. The suspension obtained is heated, with stirring, at a temperature in the vicinity of 100° C. for 7 hours and then stirred at a temperature in the vicinity of 20° C. for 16 hours. The solvent is evaporated off under reduced pressure (20 mm Hg; 2.7 kPa) at a temperature in the vicinity of 60° C. The residue is dissolved in methylene chloride (500 cc). The solution obtained is washed twice with distilled water (300 cc in total), twice with a saturated aqueous sodium bicarbonate solution (300 cc in total) and twice with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 60° C. A crude product (13.3 g) is thereby obtained, which is dissolved in boiling acetonitrile (140 cc). Decolorizing charcoal (0.5 g) is added to the solution obtained and the suspension is filtered in the heated state. The filtrate is cooled at a temperature in the vicinity of 20° C. for 2 hours. The crystals formed are separated by filtration, washed 3 times with acetonitrile (75 cc in total) add 3 times with diethyl ether (90 cc in total) and then dried under reduced pressure (20 mm Hg; 2.7 kPa) at a temperature in the vicinity of 20° C. in the presence of potassium hydroxide pellets. (+)-N-(4-methyl-2-pyridyl)-3-(3-pyridyl)-1H,3H-pyrrolo[1,2-c]thiazole-7-carboxamide (3.1 g) in the form of cream-coloured crystals, m.p. 174° C., is thereby obtained. ($[\alpha]_D^{20} = +82°\pm0.9°$; c=1.09; dimethylformamide).

The hydrochloride of the acid chloride derived from (+)-3-(3-pyridyl)-1H,3H-pyrrolo[1,2-c]thiazole-7-carboxylic acid is prepared as follows: a suspension of (+)-3-(3-pyridyl)-1H,3H-pyrrolo[1,2-c]thiazole-7-carboxylic acid (20.9 g) in a mixture of thionyl chloride (52.1 g), dimethylformamide (0.1 cc) and 1,2-dichloroethane (290 cc) is heated to a temperature in the vicinity of 80° C. for 3 hours. After cooling to a temperature in the vicinity of 20° C., the crystals are separated by filtration, washed 3 times with 1,2-dichloroethane (150 cc in total), 3 times with diethyl ether (150 cc) and then dried under reduced pressure (20 mm Hg; 2.7 kPa) at a temperature in the vicinity of 20° C. Hydrochloride of the acid chloride derived from (+)-3-(3-pyridyl)-1H,3H-pyrrolo[1,2-c]-thiazole-7-carboxylic acid (24.5 g) in the form of cream-coloured crystals, m.p. 175° C., is thereby obtained.

The (+)-3-(3-pyridyl)-1H,3H-pyrrolo[1,2-c]thiazole-7-carboxylic acid may be obtained as follows, according to one or the other of the following methods:

A. First method: a solution of ethyl (+)-3-(3-pyridyl)-1H,3H-pyrrolo[1,2-c]thiazole-7-carboxylate (19.5 g) and potassium hydroxide pellets (11.9 g) in a mixture of ethanol (70 cc) and distilled water (70 cc) is heated at a temperature in the vicinity of 40° C. for 14 hours. The solvent is evaporated off under reduced pressure (20 mm Hg; 2.7 kPa) at a temperature in the vicinity of 40° C. The residue is dissolved in distilled water (200 cc) and the solution obtained is adjusted to a pH in the region of 4 by adding an aqueous 1N hydrochloric acid solution (250 cc) and stirred at a temperature in the vicinity of 20° C. for 1 hour. The crystals formed are separated by filtration, washed 5 times with distilled water (250 cc in total), 5 times with ethanol (150 cc in total) and 3 times with diethyl ether (90 cc in total) and then dried under reduced pressure (20 mm Hg; 2.7 kPa) at a temperature in the vicinity of 20° C. in the presence of potassium hydroxide pellets. A crude product (14.1 g) with a melting point of 210° C. is thereby obtained. This product is dissolved in boiling ethanol (420 cc); decolorizing charcoal (0.5 g) is added to the solution obtained and the suspension is filtered in the heated state. The filtrate is cooled at a temperature in the vicinity of 4° C. for 16 hours. The crystals formed are separated by filtration, washed 3 times with ethanol (90 cc in total) and 3 times with diethyl ether (150 cc in total) and then dried under reduced pressure (20 mm Hg; 2.7 kPa) at a temperature in the vicinity of 20° C. (+)-3-(3-pyridyl)-1H,3H-pyrrolo[1,2-c]thiazole-7-carboxylic acid (10.3 g) in the form of cream-coloured crystals, m.p. 210° C., is thereby obtained. $[\alpha]_D^{20} = +163° \pm 1.6°$ (c=1.08; 1N sodium hydroxide).

The ethyl (+)-3-(3-pyridyl)-1H,3H-pyrrolo[1,2-c]thiazole-7-carboxylate may be prepared as follows: Triethylamine (11.2 g) is added, at a temperature between 20° and 27° C., to a suspension of (2R,4R)-N-formyl-2-(3-pyridyl)thiazolidine-4-carboxylic acid (23.8 g) in 1,2-dichloroethane (90 cc) in the course of 2 minutes. The suspension obtained is stirred at a temperature in the vicinity of 20° C. for 1 hour and the solution obtained is added, at a temperature in the vicinity of 20° C., to a solution of para-toluenesulphonyl chloride (21 g) in 1,2-dichloroethane (110 cc), in the course of 50 minutes. A turbid solution (solution A) is obtained. In a separate operation, triethylamine (33.4 g) is added, at a temperature between 20° and 30° C., to a solution of ethyl 2,3-dichloropropionate (18.6 g) in 1,2-dichloroethane (100 cc), in the course of 15 minutes. The solution A previously prepared is added, at a temperature between 20° and 36° C., to the suspension (suspension B) obtained which is stirred at a temperature in the vicinity of 20° C. for 50 minutes, in the course of 50 minutes. The suspension obtained is stirred for 1 hour and 40 minutes at a temperature in the vicinity of 40° C. and then at a temperature in the vicinity of 60° C. for 20 minutes. Distilled water (100 cc) is added to the suspension obtained after cooling it to a temperature in the vicinity of 20° C. The organic phase is separated, washed 3 times with distilled water (300 cc in total), twice with a saturated aqueous sodium bicarbonate solution (300 cc in total) and then twice with distilled water (300 cc in total), dried over anhydrous magnesium sulphate, treated with decolorizing charcoal (0.5 g), filtered and concentrated to dryness under reduced pressure (20 mm Hg; 2. kPa) at a temperature in the vicinity of 60° C. A crude product (25.6 g) is obtained, which is dissolved in ethyl acetate (250 cc). The solution obtained is extracted 3 times with an aqueous 2N hydrochloric acid solution (300 cc in total). The aqueous extracts are combined, washed with ethyl acetate (250 cc) and adjusted to a pH in the region of 8 by adding sodium bicarbonate. The suspension obtained is extracted first with a mixture of diethyl ether (250 cc) and ethyl acetate (250 cc) and then 3 times with ethyl acetate (450 cc in total). The organic extracts are combined, washed twice with distilled water (300 cc in total), dried over anhydrous magnesium sulphate, treated with decolorizing charcoal (0.5 g), filtered, treated with silica (0.020-0.045 mm; 30 g), filtered and concentrated to dryness under reduced pressure (20 mm Hg; 2.7 kPa) at a temperature in the vicinity of 60° C. Ethyl (+)-3-(3-pyridyl)-1H,3H-pyrrolo-[1,2-c]thiazole-7-carboxylate (19.6 g) in the form of an orange-coloured oil is thereby obtained. Rf=0.5 (silica gel thin layer chromatography; eluent: ethyl acetate); $[\alpha]_D^{20} = +115° \pm 1°$ (c=1.51; dimethylformamide).

The ethyl 2,3-dichloropropionate may be prepared according to the method described in Japanese Patent No. 81/87,531 [Chem. Abstr., 95, 203335, (1981)].

The (2R,4R)-N-formyl-2-(3-pyridyl)thiazolidine-4-carboxylic acid may be obtained as follows: acetic anhydride (340 g) is added, at a temperature in the vicinity of 10° C., to formic acid (420 cc), in the course of 25 minutes. The solution obtained is stirred at a temperature in the vicinity of 10° C. for 30 minutes and (2RS, 4R)-2-(3-pyridyl)thiazolidine-4-carboxylic acid (233 g) is then added to it at a temperature in the vicinity of 10° C., in the course of 50 minutes. The solution obtained is stirred at a temperature in the vicinity of 10° C. for 30 minutes and then at a temperature in the vicinity of 20° C. for 16 hours. The solvent is evaporated off under reduced pressure (20 mm Hg; 2.7 kPa) at a temperature in the vicinity of 60° C. The residue obtained is suspended in boiling ethanol (2600 cc). The suspension obtained is cooled at a temperature in the vicinity of 4° C. for 2 hours. The crystals formed are separated by filtration, washed twice with ethanol cooled to a temperature in the vicinity of 4° C. (530 cc) and air-dried. A product (245 g) melting at 230° C. is thereby obtained. A part of this product (60 g) is dissolved in boiling 50% aqueous ethanol (540 cc). The solution obtained is cooled at a temperature in the vicinity of 10° C. for 2 hours. The crystals formed are separated by filtration, washed 3 times with ethanol (300 cc in total) and 3 times with diethyl ether (450 cc in total) and then dried under reduced pressure (20 mm Hg; 2.7 kPa) at a temperature in the vicinity of 20° C. in the presence of potassium hydroxide pellets. (2R,4R)-N-formyl-2-(3-pyridyl)-thiazolidine-4-carboxylic acid (48.2 g) in the form of white crystals, m.p. 250° C., is thereby obtained. $[\alpha]_D^{20} = +100° \pm 1°$ (c=1.37; 1N sodium hydroxide).

The (2RS,4R)-2-(3-pyridyl)thiazolidine-4-carboxylic acid may be prepared according to A. BANASHEK and M. I. SHCHUKINA, J. Gen. Chem. U.S.S.R., 31, 1374 (1961); Chem. Abstr. 55, 24739h, (1961).

B. Second method: (+)-3-(3-pyridyl)-1H,3H-pyrrolo[1,2-c]thiazole-7-carboxylic acid (200 g) and L(−)-α-methylbenzylamine (147 g) are dissolved in boiling isopropanol (1000 cc). Decolorizing charcoal (0.5 g) is added to the solution obtained and the suspension is filtered in the heated state. The filtrate is cooled at a temperature in the vicinity of 20° C. for 16 hours. The crystals formed are separated by filtration, washed 3 times with isopropanol cooled to a temperature in the vicinity of 4° C. (450 cc in total) and 3 times with diethyl ether (600 cc in total) and then dried under reduced pressure (20 mm Hg; 2.7 kPa) at a temperature in the vicinity of 20° C. in the presence of potassium hydroxide pellets. A product (134.6 g) is obtained, which is dissolved in boiling isopropanol (500 cc). Decolorizing charcoal (0.5 g) is added to the solution obtained and the suspension is filtered in the heated state. The filtrate is cooled at a temperature in the vicinity of 20° C. for 16 hours. The crystals formed are separated by filtration, washed 3 times with isopropanol cooled to a temperature in the vicinity of 4° C. (300 cc in total) and twice with diethyl ether (400 cc) and then dried under reduced pressure (20 mm Hg; 2.7 kPa) at a temperature in the vicinity of 20° C. in the presence of potassium hydroxide pellets. A product (88.3 g) is obtained, which is dissolved in boiling isopropanol (500 cc); the solution obtained is filtered in the heated state and the filtrate is cooled at a temperature in the vicinity of 4° C. for 16 hours. The crystals formed are separated by filtration, washed twice with isopropanol cooled to a temperature in the vicinity of 4° C. (100 cc in total) and 3 times with diethyl ether (300 cc in total) and then dried under reduced pressure (20 mm Hg; 2.7 kPa) at a temperature in the vicinity of 20° C. in the presence of potassium hydroxide pellets. L(−)-α-methylbenzylamine salt of (+)-3-(3-pyridyl)-1H,3H-pyrrolo[1,2-c]thiazole-7-carboxylic acid (77.3 g) in the form of cream-coloured crystals, m.p. 154° C., is thereby obtained. $[\alpha]_D^{20} = +110° \pm 2°$ (c=1.01; water).

This product is dissolved in distilled water (600 cc) at a temperature in the vicinity of 65° C. The solution obtained is filtered in the heated state and cooled to a temperature in the vicinity of 10° C. and adjusted to a pH in the region of 3.5 by adding concentrated hydrochloric acid at a temperature between 10° and 15° C. The crystals formed are separated by filtration, washed 3 times with distilled water (600 cc in total), twice with ethanol (160 cc in total) and twice with diethyl ether (200 cc in total) and then dried under reduced pressure (20 mm Hg; 2.7 kPa) at a temperature in the vicinity of 20° C. in the presence of potassium hydroxide pellets. A product (48 g) is obtained, which is dissolved in boiling ethanol (1000 cc); decolorizing charcoal (0.5 g) is added to the solution obtained and the suspension is filtered in the heated state. The filtrate obtained is cooled at a temperature in the vicinity of 4° C. for 2 hours. The crystals formed are separated by filtration, washed twice with ethanol cooled to a temperature in the vicinity of 4° C. (60 cc in total), then twice with diethyl ether (200 cc) and then dried under reduced pressure (20 mm Hg; 2.7 kPa) at a temperature in the vicinity of 20° C. in the presence of potassium hydroxide pellets. (+)-3-(3-pyridyl)-1H,3H-pyrrolo[1,2-c]thiazole-7-carboxylic acid (42.5 g) in the form of yellow crystals, m.p. 210° C., is thereby obtained. $[\alpha]_D^{20} = +168° \pm 2°$ (c=1.02; 1N NaOH).

The (±)-3-(3-pyridyl)-1H,3H-pyrrolo[1,2-c]thiazole-7-carboxylic acid may be prepared according to the method described in European Patent No. 0,115,979.

EXAMPLE 11

7-Chloroformyl-3-(3-pyridyl)-1H,3H-pyrrolo[1,2-c]thiazole hydrochloride (6 g) is added, at a temperature between 60° and 70° C., to a solution of 2-amino-4,6-dimethylpyridine (2.4 g) and triethylamine (4.1 g) in dioxane (100 cc) which is heated to a temperature in the vicinity of 60° C., in the course of 25 minutes. The suspension obtained is heated, with stirring, at a temperature in the vicinity of 100° C. for 5 hours and 30 minutes and then stirred at a temperature in the vicinity of 20° C. for 16 hours. The solvent is evaporated off under reduced pressure (20 mm Hg; 2.7 kPa) at a temperature in the vicinity of 50° C. The residue is dissolved in methylene chloride (400 cc). The solution obtained is washed with distilled water (100 cc), twice with an aqueous 1N sodium hydroxide solution (200 cc in total) and 3 times with distilled water (300 cc in total) and then dried over anhydrous magnesium sulphate, treated with decolorizing charcoal (0.5 g), filtered and concentrated to dryness under reduced pressure (20 mm Hg; 2.7 kPa) at a temperature in the vicinity of 50° C. A crude product (6.3 g) is thereby obtained, which is dissolved in boiling acetonitrile (140 cc). Decolorizing charcoal (0.5 g) is added to the solution obtained and the suspension is filtered in the heated state. The filtrate is cooled at a temperature in the vicinity of 20° C. for 1 hour. The crystals formed are separated by filtration, washed twice with acetonitrile cooled to a temperature in the vicinity of 4° C. (20 cc in total) and then dried under reduced pressure (20 mm Hg; 2.7 kPa) at a temperature in the vicinity of 20° C. in the presence of potassium hydroxide pellets. N-(4,6-dimethyl-2-pyridyl) 3-(3-pyridyl)-1H,3H-pyrrolo-[1,2-c]thiazole-7-carboxamide (3.9 g) in the form of white crystals, m.p. 171° C., is thereby obtained.

The 7-chloroformyl-3-(3-pyridyl)-1H,3H-pyrrolo[1,2-c]thiazole hydrochloride is prepared according to the method described in European patent No. 0,115,979.

The present invention also provides a pharmaceutical composition which comprises a compound according to the invention and a compatible and pharmaceutically acceptable diluent or adjuvant. The composition may also contain other pharmaceutically compatible products which may be inert or physiologically active. These pharmaceutical products may be administered orally, parenterally, rectally or locally.

Tablets, pills, powders (especially in gelatin capsules or wafer capsules) or granules may be used as solid compositions for oral administration. In these compositions, the compound according to the invention is mixed with one or more inert diluents such as starch, cellulose, sucrose, lactose or silica. These compositions may also contain substances other than diluents, e.g. one or more lubricants such as magnesium stearate, talcum, a colour, a coating (dragees) or a lacquer.

Pharmaceutically acceptable solutions, suspensions, emulsions, syrups and elixirs containing inert diluents such as water, ethanol, glycerol, vegetable oils or liquid paraffin may be used as liquid compositions for oral administration. These compositions may also contain substances other than diluents, e.g. wetting agents, sweeteners, thickeners, flavouring agents or stabilizers.

Sterile compositions for parenteral administration may preferably be aqueous or non-aqueous solutions, suspensions or emulsions. Water, propylene glycol, a polyethylene glycol, vegetable oils, especially olive oil, injectable organic esters, e.g. ethyl oleate or other suitable organic solvents may be used as the solvent or the vehicle.

These compositions may also contain adjuvants, especially wetting agents, tonicity regulating agents, emulsifiers, dispersants and stabilizers. The sterilization may be carried out in several ways, e.g. by aseptizing filtration, by incorporating sterilizing agents into the composition, by radiation or by heating. They may also be prepared in the form of sterile solid compositions which can be dissolved in an injectable sterile medium at the time of use.

The compositions for rectal administration are suppositories or rectal capsules, which contain, in addition to the active product, excipients such as cocoa butter, semisynthetic glycerides or polyethylene glycols.

The compositions for local application may be e.g. creams, ointments, lotions, eye lotions, mouthwashes, nasal drops or aerosols.

In human therapeutics, the pharmaceutical products according to the invention are particularly useful in the treatment of all pathological conditions in which PAF-acether may be directly or indirectly implicated, especially allergic and inflammatory conditions and complaints of the digestive system such as ulcers, colitises and intestinal lesions caused by radiation or endotoxin-induced shocks. The doses depend on the effect sought and the period of treatment; they are generally between 25 and 300 mg per day, taken in a single dose or in split doses, by the oral or the intraveneous route or by inhalation, for an adult.

In general, the medical practitioner will determine the dose that he considers most appropriate depending on age, weight and all the other factors specific to the subject under treatment.

The following examples illustrate the composition according to the invention.

EXAMPLE A

Tablets containing a 25 mg dose of the active product, with the following composition, are prepared according to the conventional technique:

| | |
|---|---|
| N—(6-chloro-2-pyridyl)-3-(3-pyridyl)-1H,3H—pyrrolo-[1,2-c]thiazole-7-carboxamide | 25 mg |
| Starch | 60 mg |
| Lactose | 50 mg |
| Magnesium stearate | 2 mg |

EXAMPLE B

An injectable solution containing 5 mg of the active product, with the following composition, is prepared according to the conventional technique:

| | |
|---|---|
| (+)-N—(4-methyl-2-pyridyl)-3-(3-pyridyl)-1H,3H—pyrrolo[1,2-c]thiazole-7-carboxamide | 5 mg |
| 0.01 N hydrochloric acid solution | 0.29 cc |
| Injectable aqueous solution | 2 cc |

We claim:

1. A compound of the general formula I:

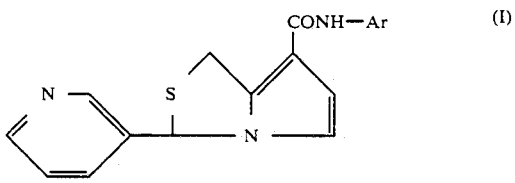

in which Ar is a pyridyl substituted with one or more halogen or alkyl, alkyloxy, alkylthio, trifluoromethyl, amino, alkylamino, dialkylamino, hydroxy, cyano, alkylsulphinyl, alkylsulphonyl, sulphamido, alkylsulphamido, dialkylsulphamido, alkylcarbonyl, benzoyl, alkyloxycarbonyl, carboxy, phenoxycarbonyl, alkylcarbonyloxy, benzoyloxy, alkylcarbonylamino, benzamido, phenyl, benzyl, phenoxy or phenylthio group, provided that (i) an alkyl moiety contains 1 to 4 straight- or branched chain carbon atoms; (ii) a phenyl moiety may be unsubstituted or substituted with one or more halogen or alkyl, alkyloxy, alkylthio, trifluoromethly, amino, alkylamino, dialkylamino, hydroxy, cyano, phenyl or benzyl group in separate enantiomeric form or mixtures thereof; or a pharmaceutically acceptable salt thereof.

2. A pharmaceutical composition useful in the treatment of the adverse effects of PAF acether which comprises an effective amount of a compound as defined in claim 1 and a compatible and pharmaceutically acceptable diluent or adjuvant.

3. A compound as claimed in claim 1 in which Ar is a pyridyl group substituted by one or more halogen, or alkyl or alkoxy groups.

4. A compound as claimed in claim 1 which is in the dextrorotatory form.

5. A compound as claimed in claim 1 which is (+)-N-(4-methyl-2-pyridyl)-3-(3-pyridyl)-1H,3H-pyrrolo[1,2-c]thiazole-7-carboxamide.

6. A compound as claimed in claim 1 which is N-(4-methyl-2-pyridyl)-3-(3-pyridyl)-1H,3H-pyrrolo-[1,2-c]thiazole-7-carboxamide or a pharmaceutically acceptable salt thereof.

7. A compound as claimed in claim 1 which is N-(6-chloro-2-pyridyl)-3-(3-pyridyl)-1H,3H-pyrrolo-[1,2-c]thiazole-7-carboxamide or a pharmaceutically acceptable salt thereof.

8. A compound as claimed in claim 1 which is N-(4-chloro-2-pyridyl)-3-(3-pyridyl)-1H,3H-pyrrolo-[1,2-c]thiazole-7-carboxamide or a pharmaceutically acceptable salt thereof.

9. A method of treatment of the adverse effects of P.A.F-acether comprising administering to a subject suffering therefrom or liable thereto, an effective dose of a compound as claimed in claim 1.

10. A method of treatment of the adverse effects of P.A.F.-acether comprising administering to a subject suffering therefrom or liable thereto an effective dose of a composition as claimed in claim 2.

11. A method according to claim 10 in which the dose is from 25 to 300 mg per day of compound of general formula I or pharmaceutically acceptable salt thereof.

12. A method according to claim 10 in which the treatment is administered orally, intravenously or by inhalation.

* * * * *